US009333281B2

(12) United States Patent
Giezendanner et al.

(10) Patent No.: US 9,333,281 B2
(45) Date of Patent: May 10, 2016

(54) DRAINAGE PUMP UNIT

(75) Inventors: Charles Giezendanner, Morschach (CH); Martin Melzer, Cham (CH)

(73) Assignee: MEDELA HOLDING AG, Baar (CH)

( * ) Notice: Subject to any disclaimer, the term of this patent is extended or adjusted under 35 U.S.C. 154(b) by 835 days.

(21) Appl. No.: 13/351,077

(22) Filed: Jan. 16, 2012

(65) Prior Publication Data

US 2012/0184932 A1 Jul. 19, 2012

(30) Foreign Application Priority Data

Jan. 17, 2011 (CH) ........................................ 0078/11

(51) Int. Cl.
*A61M 1/00* (2006.01)
*G01F 23/26* (2006.01)

(52) U.S. Cl.
CPC ............ *A61M 1/0023* (2013.01); *A61M 1/0025* (2014.02); *A61M 1/0066* (2013.01); *G01F 23/266* (2013.01); *G01F 23/268* (2013.01); *A61M 2205/3382* (2013.01); *A61M 2205/3386* (2013.01)

(58) Field of Classification Search
CPC ............ A61M 1/0023; A61M 1/0031; A61M 1/0005; A61M 1/00; A61M 1/0011; A61M 1/0066; A61M 2205/3389; A61M 2205/3379; G01F 23/266; G01F 23/268; G01F 23/263; G01F 23/26; G01F 23/265; G01F 23/242
USPC ...... 73/290 R, 304 C, 304 R, 61.61; 604/319, 604/315, 35, 67
See application file for complete search history.

(56) References Cited

U.S. PATENT DOCUMENTS 4,092,860 A * 6/1978 Arts et al. .................... 73/304 R
4,099,167 A * 7/1978 Pomerantz et al. ........... 340/620

5,747,689 A * 5/1998 Hampo et al. ............... 73/304 C
8,469,050 B2 * 6/2013 King .................... A61M 1/0058
137/392
2005/0172712 A1 * 8/2005 Nyce ..................... G01F 23/268
73/304 C
2008/0033386 A1 * 2/2008 Okabe et al. .................. 604/378
2009/0157016 A1 * 6/2009 Adahan ............... A61M 1/0001
604/290

(Continued)

FOREIGN PATENT DOCUMENTS

| DE | 19645970 | 5/1998 |
| EP | 0853950 | 7/1998 |
| JP | 2161322 | 6/1990 |
| WO | 2006/021295 | 3/2006 |

(Continued)

OTHER PUBLICATIONS

Swiss Search Report for Swiss Patent App. No. 0078/11, dated Apr. 18, 2011.

*Primary Examiner* — John Fitzgerald
*Assistant Examiner* — Marrit Eyassu
(74) *Attorney, Agent, or Firm* — McDonnell Boehnen Hulbert & Berghoff LLP

(57) ABSTRACT

A drainage pump unit for aspirating body fluids by means of a suction pump has a suction pump arranged in a suction pump housing, wherein a fluid collection container can be secured releasably on the suction pump housing, and wherein a capacitive filling level sensor is arranged on the suction pump housing for detecting a filling level in the fluid collection container. The filling level sensor has at least two electrodes, which are arranged at a distance from each other and extend along a common path. A first of the electrodes is in one piece, and a second of the electrodes is segmented. This arrangement permits the production of inexpensive fluid collection containers while still ensuring a high degree of measurement accuracy.

17 Claims, 5 Drawing Sheets

(56) References Cited

U.S. PATENT DOCUMENTS

2009/0163882 A1* 6/2009 Koch et al. .................... 604/319
2010/0071459 A1* 3/2010 Kamm et al. ................ 73/304 C
2010/0126268 A1* 5/2010 Baily et al. .................. 73/304 C
2011/0040288 A1* 2/2011 Eckstein et al. .............. 604/543
2013/0286615 A1* 10/2013 Inagaki et al. ................ 361/767

FOREIGN PATENT DOCUMENTS

| WO | 2007/128156 | 11/2007 |
| WO | 2008/119993 | 10/2008 |
| WO | 2008/141471 | 11/2008 |
| WO | 2009/098077 | 8/2009 |

* cited by examiner

DRAINAGE PUMP UNIT

CROSS REFERENCE TO RELATED APPLICATIONS

The present application claims priority to Swiss Application No. 0078/11 filed on Jan. 17, 2011, the contents of which is incorporated herein by reference in its entirety.

TECHNICAL FIELD

The present invention relates to a drainage pump unit.

BACKGROUND

Drainage pump systems are used to aspirate body liquids and fluids in the medical field. For example, they are used during or after surgical interventions, in wound drainage, in thorax drainage or in liposuction. These drainage pump systems usually have a vacuum pump, one or more fluid collection containers, and a drainage tube connection between patient and fluid collection container. The fluid collection container can be secured releasably on the housing of the drainage pump or connected to the pump via an external vacuum tube.

With an underpressure being generated in the fluid collection container by means of the suction pump or vacuum pump, the fluid or secretion from a cavity in the patient can be aspirated through the drainage or secretion tube and into the collection container and collected therein. Filters arranged on the pump-side outlet of the collection container protect the suction pump from possible contamination by the aspirated fluid. Drainage pump systems of this kind are disclosed in WO 2007/128156 and WO 2008/141471, for example. The drainage pump systems described there are portable.

Capacitive filling level sensors are suitable for the purpose of monitoring the drainage process and the filling level of the fluid collection container.

Filling level sensors are known in the prior art. Thus, U.S. Pat. No. 4,099,167 discloses a capacitive filling level sensor for determining a filling level of a liquid container. In one embodiment, the filling level sensor has a band-shaped first electrode, and several second electrodes spaced apart from the first electrode. The second electrodes are spaced apart from one another in the vertical direction. The first electrode and also the second electrodes are arranged on the outer face of the container. Third band-shaped electrodes are arranged in the horizontal direction inside the container and extend from the first electrode to the second electrodes. In a further embodiment, only the first electrode and the second electrodes are present, the container in this case being designed with a double wall. The first electrode is located on the outer face of the outer wall, and the second electrodes are arranged on the outer face of the inner wall.

U.S. Pat. No. 5,747,689 describes a filling level sensor that is partially immersed in a liquid container. The sensor has two plates extending parallel to each other and spaced apart from each other. One of the plates is segmented, and the individual segments are spaced apart from one another.

JP 2161322 discloses a capacitive filling level sensor with two electrodes, wherein a first electrode is mounted on the outer wall of a container and the second electrode forms a tube piece, through which water flows out of the container.

U.S. Pat. No. 4,092,860 discloses a capacitive filling level sensor mounted on the outer face of a connector piece and composed of several band-shaped electrodes. This sensor is protected from the outside by a Teflon® coating.

DE 196 45 970 discloses a band-shaped capacitive filling level sensor in the form of a flat ribbon cable. The capacitive sensor elements are formed by cores of the flat ribbon cable. The sensor is arranged in the interior of a container.

WO 2009/098077 discloses a capacitive filling level sensor in a measuring container, wherein the sensor comprises segments.

In drainage systems for aspirating body liquids, the filling level sensors are usually located on or in the fluid collection container. Thus, WO 2008/119993 discloses a fluid collection container with a filling level sensor mounted on the outer face of the container. The sensor comprises several band-shaped plates, which are arranged in the vertical and horizontal directions on the container.

EP 0 853 950 discloses a drainage pump unit with a suction unit and with a fluid collection container, where a capacitive filling level sensor is arranged on the suction unit.

For hygiene reasons, fluid collection containers can only be used for a limited time and should therefore be as inexpensive as possible. If the filling level sensors are mounted on the fluid collection container, however, the costs increase. By contrast, filling level sensors mounted on the drainage pump unit have less precision than filling level sensors mounted on the container, particularly in the case of small filling quantities, and particularly in the case of non-homogeneous liquids.

SUMMARY

It is therefore an object of the invention to make available a drainage pump unit that eliminates the abovementioned disadvantages.

The drainage pump unit according to the invention for aspirating body fluids by means of a suction pump has a suction pump arranged in a suction pump housing. A fluid collection container can be secured releasably on the suction pump housing. Moreover, a capacitive filling level sensor is arranged on the suction pump housing for the purpose of detecting a filling level in the fluid collection container. According to the invention, the filling level sensor has at least two electrodes, which are arranged at a distance from each other and extend along a common path. At least one of these electrodes is segmented. At least one of the electrodes is in one piece, and at least one other of the electrodes is segmented. However, it is also possible for all the additional electrodes to be segmented. The one-piece electrode is a transmitter electrode, and the segmented second electrode is a receiver electrode. An excitation signal can be applied by a modulator to the one-piece first electrode.

The excitation signal can be coupled capacitively into the segmented second electrode.

The arrangement of the filling level sensor on the suction pump housing allows the costs of the fluid collection containers to be kept as low as possible.

By using a filling level sensor with at least one segmented electrode, the measurement accuracy is sufficiently high despite the arrangement on the suction pump housing. The segmented electrode, particularly when designed as a receiver electrode, helps compensate for variations in the measured signal level. In the case of several segments, it is possible to measure the ratio of the signals of the different segments to one another. It is thus possible to compensate for influences played by properties of the liquid and by environmental effects, for example the presence of metal in the area surrounding the pump. The segmented electrode also permits measurements of the filling level at intermediate heights. Thus, not only an empty or full container can be detected.

The electrodes preferably extend along approximately an entire fillable height of the container. By virtue of this filling level sensor, it is also possible to gain information concerning the filling speed or filling rate of the fluid collection container.

In a preferred embodiment, at least two of the electrodes, preferably all of the electrodes, are arranged next to each other in a common plane, in which case the electrodes are preferably oriented in the same direction. The electrodes are preferably arranged in or on a wall of the suction pump housing, the wall faces towards the fluid collection container in the intended position of use. Preferably, the wall touches the fluid collection container, or a very small air gap is present between wall and fluid collection container.

In another embodiment, a first electrode is arranged on a side lying opposite a second electrode such that the first and second electrodes face each other. Both electrodes in this case are preferably arranged in a respective wall, and both walls face towards the fluid collection container. In particular, the walls touch the fluid collection container, or there is only a very small air gap between them.

In a preferred embodiment, the segmented electrode is divided into segments, which are electrically insulated from one another and are arranged with a spacing of less than 1 mm between one another. This practically contiguous juxtaposition of the segments increases the accuracy of the filling level detection. Preferably, the electrode is divided into more than three or four segments, and in one example into precisely eight segments. The segments are preferably all the same height. However, the segments can also have different heights.

In a preferred embodiment, an electronics system is present, by means of which a first electrode can be excited with an oscillating signal, particularly in a sinusoidal function. The excitation of the first electrode preferably takes place at a frequency in the range of 4 to 5 MHz. It has been found that, in this frequency range, a measurement signal can be obtained that is generally independent of the nature of the secretion collected in the fluid collection container. In particular, a frequency of at least approximately 4 MHz or of 4.75 MHz has yielded good results.

In order to compensate in the best possible way, even in the case of low filling levels, for influences exerted on the measurement signal by properties of the liquid and by environmental effects, it is also possible to use a further excitation. The latter is preferably approximately 100 kHz.

In a preferred embodiment, the electrodes are band-shaped. The segments of the segmented electrode are in this case preferably arranged one above another in a line. However, they can also be arranged one above another in an offset configuration.

The electrodes are preferably copper-coated circuit boards.

The filling level sensor is easy to incorporate in the suction pump housing if the electrodes are arranged on the same printed circuit board. Preferably, the electronics system of the sensor, including a microprocessor for evaluating the signal, is also located on the printed circuit board.

In one embodiment, the two electrodes are arranged on an outer face of the suction pump housing. It is also possible for one of the electrodes to be arranged on the outer face and the other electrode on the inner face. Preferably, however, the electrodes are arranged individually or on the common printed circuit board on an inner wall of the suction pump housing, i.e. on the inner face. This protects the sensitive electrode surfaces from external stress, for example when exchanging the fluid collection container.

Assembly is simplified, and the sensor optimally protected, if the inner wall of the suction pump housing has a depression for receiving the electrodes, the depression being dimensioned so that the electrodes do not protrude from the inner wall in the direction of the container interior. Preferably, the rear face of the electrodes or of the printed circuit board is flush with the edge face of the inner wall.

A further advantage of the drainage pump unit according to the invention is that a single filling level sensor can be used without special adaptations for containers of different shapes or containers of different sizes.

Other embodiments are set forth in the dependent claims.

BRIEF DESCRIPTION OF THE FIGURES

Preferred embodiments of the invention are described below with reference to the drawings, which serve only for explanatory purposes and are not to be interpreted as limiting the invention. In the drawings.

DETAILED DESCRIPTION

Figure 1:
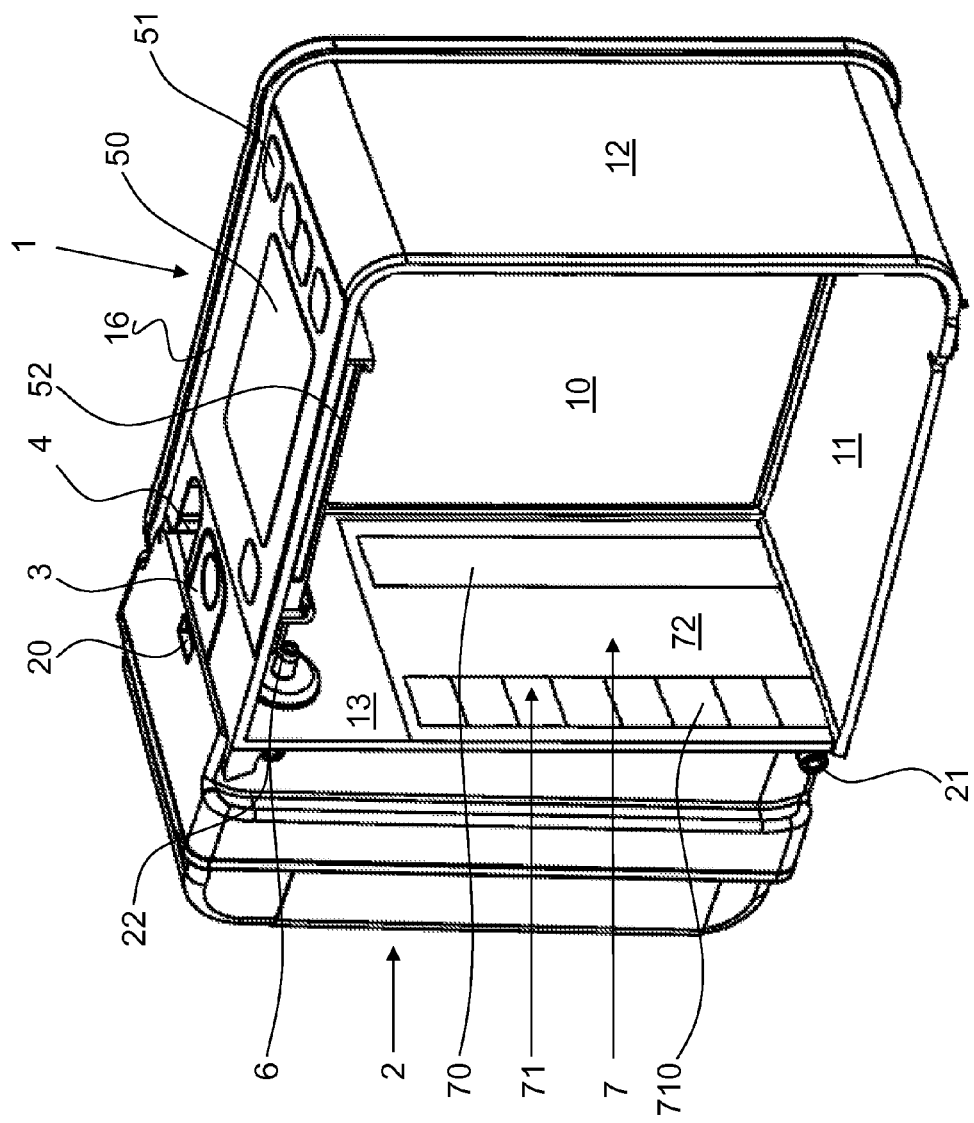
FIG. 1 shows a perspective schematic view of a first embodiment of a drainage pump unit according to the invention, with open housing.
Figure 2:
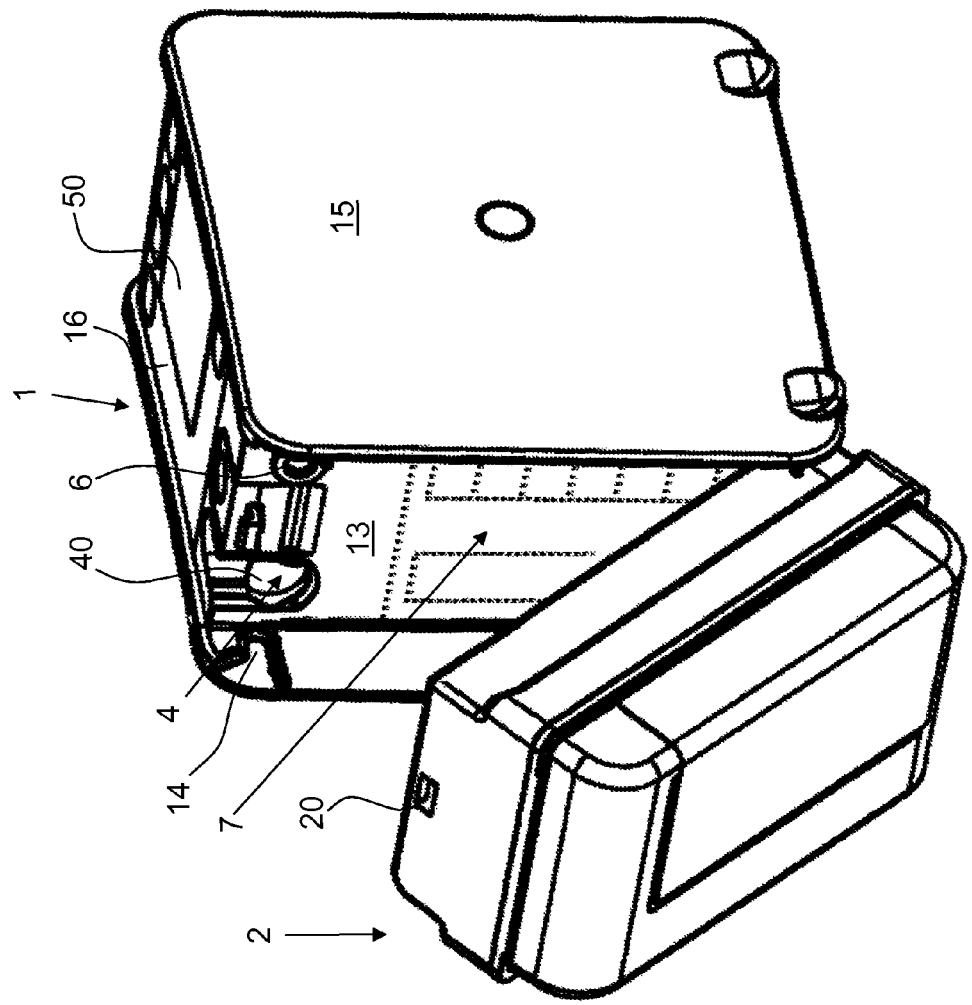
FIG. 2 shows another perspective view of the drainage pump unit according to FIG. 1, with the fluid collection container swivelled partly away.

FIGS. 1 and 2 show a drainage pump unit, as is known in principle from WO 2007/128156 and WO 2008/141471, for example. The pump unit is used for aspirating body liquids or body fluids in the medical field and are preferably portable. In other words, the patient is able to move around freely during the pumping.

The drainage pump unit has a suction pump housing 1 with a back wall 10, a bottom 11, two side walls 12, 13, a front wall 15 and an upper wall 16. In this example, the suction pump housing 1 is cuboid, and at least one lateral outer wall of the housing, in this case the second side wall 13, is substantially flat. However, the suction pump housing 1 can also have another shape.

The housing 1 can be portable, for example by means of a carrying handle (not shown). Alternatively or in addition to the carrying handle, the housing 1 preferably has a support surface or feet, such that the housing, in the position depicted, can be placed on a table or on another suitable support surface. Comments made below regarding directions are to be interpreted in this standing position of the housing.

The housing 1 accommodates a suction pump or vacuum pump 17. The suction pump 17 can be operated via control keys 51 arranged on the housing 1. Instead of control keys, it is also possible to use switches or control panels. A display 50 shows information used for operating the pump or drainage pump unit. An electronics system 52 for controlling the pump and for controlling and/or evaluating any further elements present in the drainage pump unit is likewise arranged in the housing 1 and connected to the keys 51 and to the display 50.

The front wall 15 and the back wall 10 protrude laterally from the second side wall 13 and form, together with the second side wall 13, a receiver for a fluid collection container 2.

The fluid collection container 2 is preferably substantially cuboid. The suction pump housing 1 and the fluid collection container 2 are preferably made of plastic.

The fluid collection container 2 is secured releasably on the suction pump housing 1. the fluid collection container 2 is preferably swivelled inward and locks in this position. For this purpose, the protruding parts of the front wall 15 and of the back wall 10 have upper and lower slide guides 14 in which upper and lower locking pins 21, 22 of the fluid collection container 2 engage. The fluid collection container 2 has two mutually opposite upper and two mutually opposite lower locking pins 21, 22, which all protrude from the same outer side wall of the container 2. With this side wall, the fluid collection container 2 bears on the second side wall 13 of the suction pump housing 1, and a small air gap may be present. Preferably, the side wall of the fluid collection container 2 is likewise substantially flat.

The collection container 2 has a recess 20 in which a locking element 3, here a locking hook, arranged on the housing 1 latches, and thus releasably fixes the collection container 2 in position on the housing 1. Instead of slide guides, locking pins, and locking hooks, the securing of the collection container 2 can also be connected to the housing 1 by other means. Moreover, the physical configuration of the connection between the housing 1 and of the collection container 2 can be different.

A housing-side vacuum attachment part 6 is present in the second side wall 13 of the housing 1. The vacuum attachment part 6 is preferably arranged in an upper area of the second side wall 13. In this example, the vacuum attachment part 6 is in the form of a connector piece which engages in a corresponding opening (not shown here) of the fluid collection container 2. The free end of the connector piece 6 is flush with the second side wall 13 of the housing 1, or may be set back relative to the side wall in the direction of the housing 1. Thus, the connector piece 6 preferably does not protrude. To ensure that the vacuum connection formed by the connector piece 6 between housing 1 and container 2 is leaktight, the connector piece 6 of the housing 1 and/or the opening of the container 2 have/has a sealing ring (not shown here). To ensure that aspirated secretion collected in the container 2 cannot enter the housing 1, the vacuum attachment part 6 and/or the associated opening of the container 2 are/is preferably provided with one or more filters.

A housing-side secretion attachment part, or a recess 4 for attaching such an attachment part, is present in the upper area of the second side wall 13, on the side opposite the vacuum attachment part 6. A pump-side attachment part of a patient-side drainage tube can be plugged in here, as is disclosed in WO 2008/141471. The secretion attachment part is, like the vacuum attachment part 6, connected in a leaktight manner to a corresponding opening of the fluid collection container 2 when the fluid collection container 2 is secured on the housing 1, in this case swivelled into place. However, it is also possible for the connection between container 2 and patient-side drainage tube to be established in another way, for example by the tube also being able to be plugged in directly or via suitable coupling parts in the container 2. Moreover, a housing-side service inlet 40 is present, which can be connected to a service tube leading to the patient.

By way of the vacuum attachment part 6, an underpressure is generated in the container 2 by means of the suction pump 17. By virtue of this underpressure, a fluid or secretion is aspirated from the cavity of the patient through the drainage tube and into the container 2 and collected there.

The device according to the invention comprises at least one capacitive filling level sensor 7 by means of which the filling level in the fluid collection container 2 can be determined. The filling level sensor 7 is arranged in the second side wall 13, which faces towards the fluid collection container 2.

Figure 3:
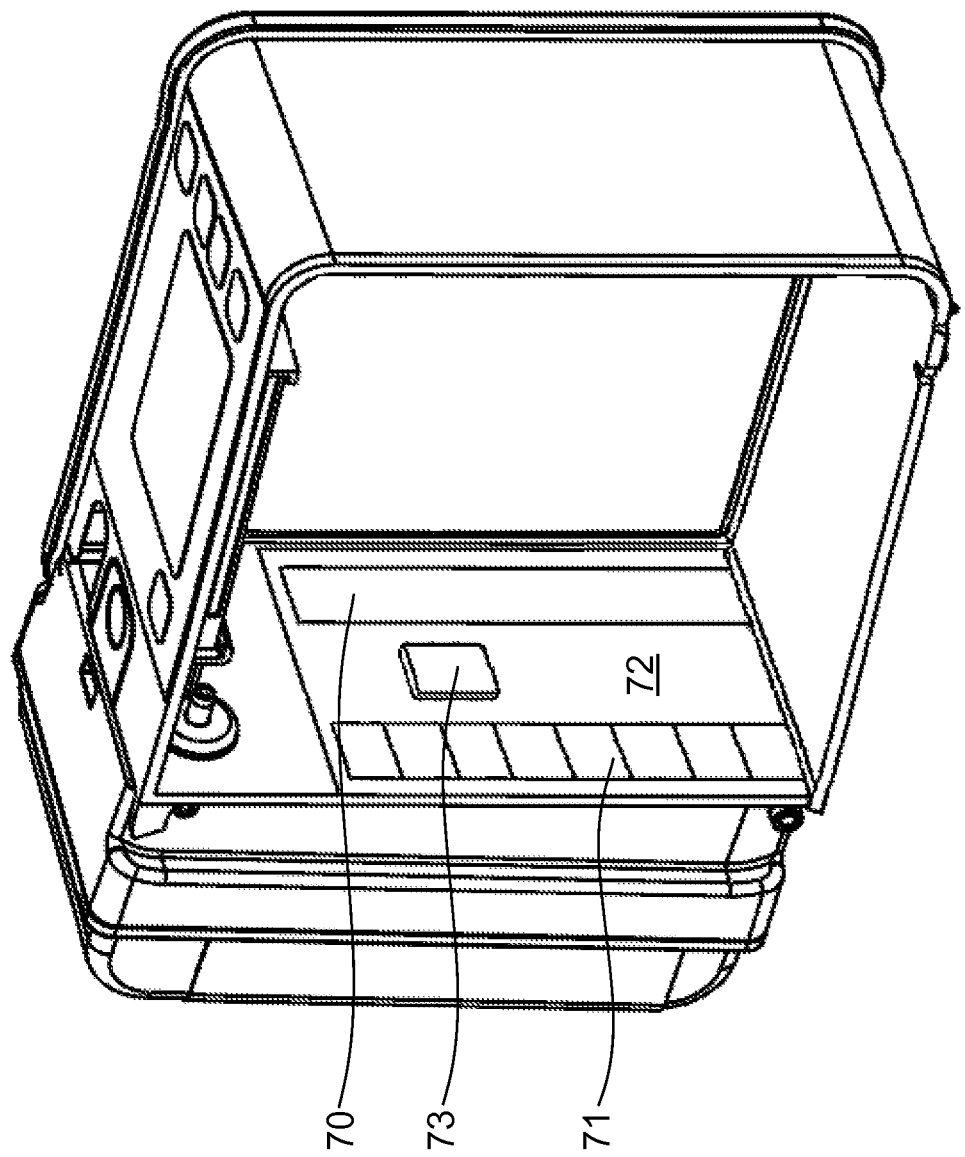
FIG. 3 shows a perspective schematic view of a second embodiment of a drainage pump unit according to the invention, with open housing.
Figure 4:
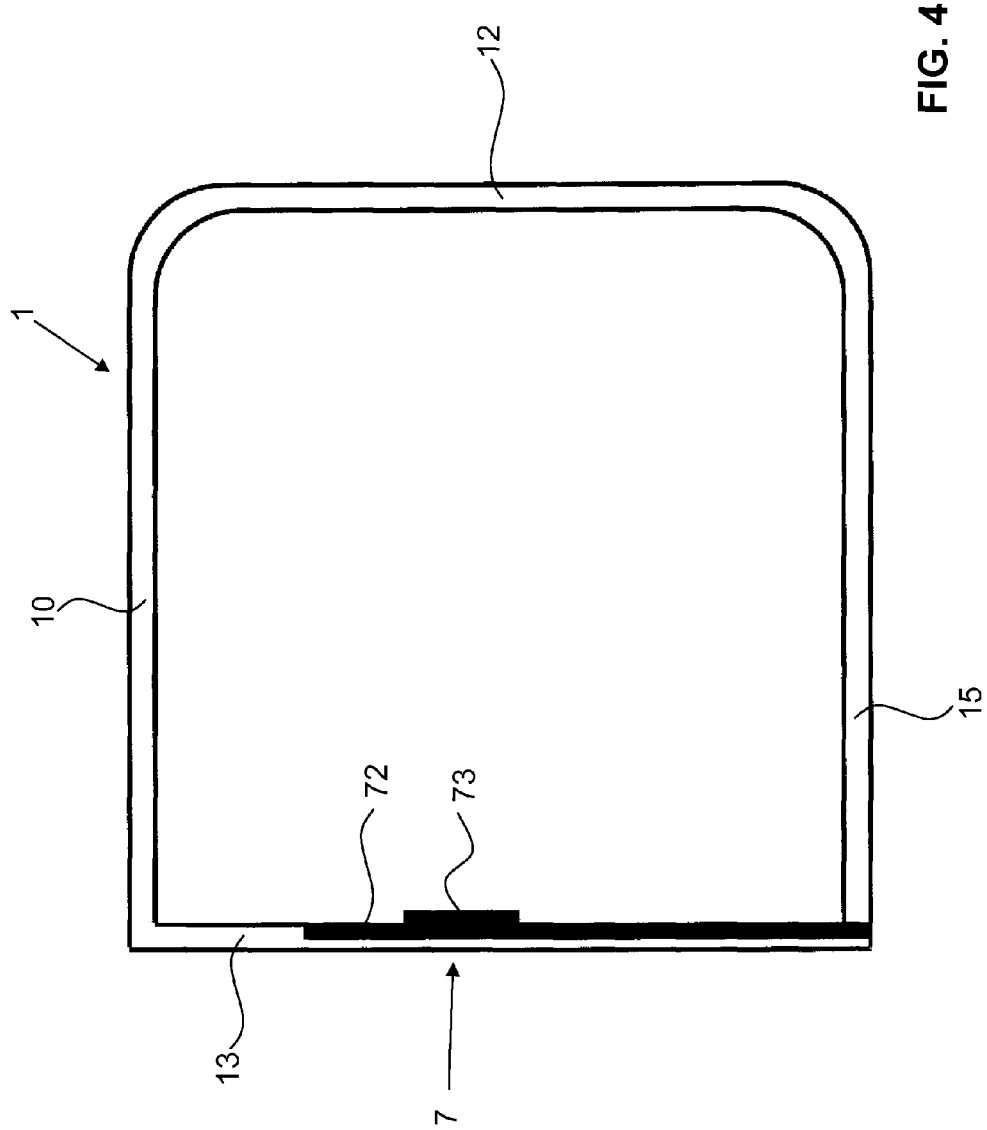
FIG. 4 shows a cross section through the drainage pump unit according to FIG. 3 without fluid collection container.

The filling level sensor 7 has at least two electrodes, and in this case precisely two electrodes. A first electrode 70 forms a transmitter, and a second electrode 71 forms a receiver for receiving the signal sent from the transmitter. A charge transfer from the transmitter electrode to the receiver electrode is determined. The two electrodes 70, 71 extend parallel to and at a distance from each other. In this example, the two electrodes are arranged in a common plane. The transmitter and receiver surfaces, respectively, are thus oriented in the same direction, namely towards the fluid collection container 2. The electrodes 70, 71 are in this case preferably arranged on the inner face of the housing 1, such that the side wall 13 lies between sensitive electrode surfaces and fluid collection container 2. The side wall 13 can be made thinner in this area or can have a window with a suitable dielectric material. A depression is preferably present on the inner face of the second side wall 13, into which depression the electrodes 70, 71 are placed jointly or individually. In this example, the electrodes 70, 71 are arranged on a common printed circuit board 72, which is let into the depression in such a way that the rear faces of the printed circuit board 72 and/or of the electrodes 70, 71 are flush with the inner face of the second side wall 13. In the illustrative embodiment according to FIGS. 3 and 4, a microprocessor 73 for operating the filling level sensor 7 is also arranged on this printed circuit board 72. This microprocessor 73 is preferably connected to the rest of the control electronics 52 of the suction pump unit 17.

Figure 6:
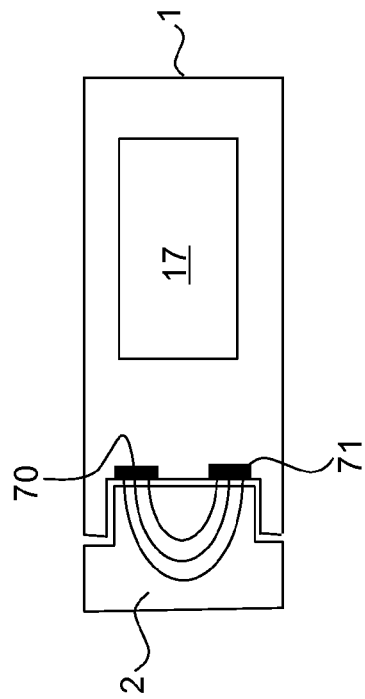
FIG. 6 shows a view illustrating a basic principle of the drainage pump unit of the invention according to the first and second embodiments.
Figure 7:
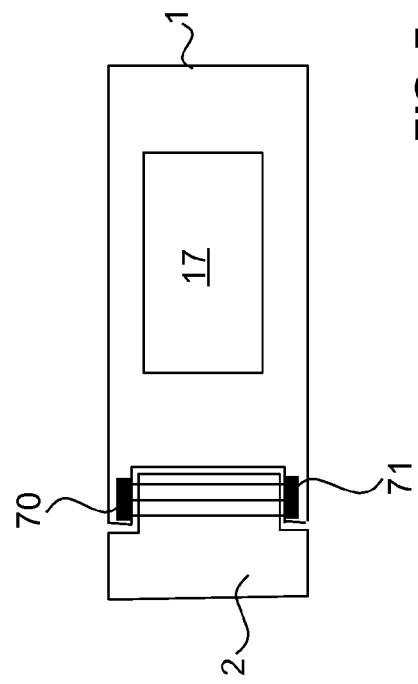
FIG. 7 shows a view illustrating a basic principle of the drainage pump unit of the invention according to a third embodiment.

The internal arrangement of the electrodes 70, 71 is shown once again in a schematic representation in FIG. 6. One of a number of further possible arrangements is shown in FIG. 7. Here, the two electrodes 70, 71 are arranged as before on the inner face or outer face of the housing 1, but lie opposite each other. In the present housing 1, this can be achieved by the electrodes 70, 71 being arranged not in the second side wall 13, but instead on or in the parts of the front wall 15 and back wall 10 protruding from the side wall 13.

The two electrodes 70, 71 are in each case band-shaped, with a length, a width and a thickness. The thickness preferably has the smallest dimension, being many times smaller than the width and length. The width of the electrodes 70, 71 is likewise substantially smaller than the length, preferably by at least one dimension. The two electrodes 70, 71 are preferably identical in terms of their overall length, width and thickness. Typical values are: thickness 35 μm; length 10 cm; width 2 cm.

The two electrodes 70, 71 are preferably formed from copper-coated circuit boards. If the electrodes are arranged on a single or common board, the board can be provided with a copper layer.

The two electrodes 70, 71 extend along a desired measurement range of the fluid collection container 2. The electrodes preferably extend approximately along the entire possible filling height of the fluid collection container 2. In this example, this corresponds to a substantial part of the height of the second side wall 13. Typical lengths are 9 cm to 15 cm. The two electrodes 70, 71 are preferably arranged with their length running in the vertical direction.

The distance of the two electrodes 70, 71 from each other is as great as possible, that is to say they are located at the outer margins of the second side wall 13 or at the outer margins of the fluid collection container 2. Typical distances are 25 to 40 mm.

The first electrode 70 is in one piece. The second electrode 71 is segmented. The second electrode 71 is preferably divided into identically sized segments 710 of the same height and preferably also of the same width. The segments 710 can be present in any desired number. There are preferably at least four segments 710. Good results were achieved with eight segments 710. The segments 710 are preferably arranged vertically one above another. In this arrangement, the segments 710 can be arranged in a line or offset in relation to one another. The segments 710 are juxtaposed as far as possible without spacing, any spacing being preferably formed only by an electrical insulation. This spacing is therefore relatively small and is preferably a maximum of 1 mm.

Figure 5:
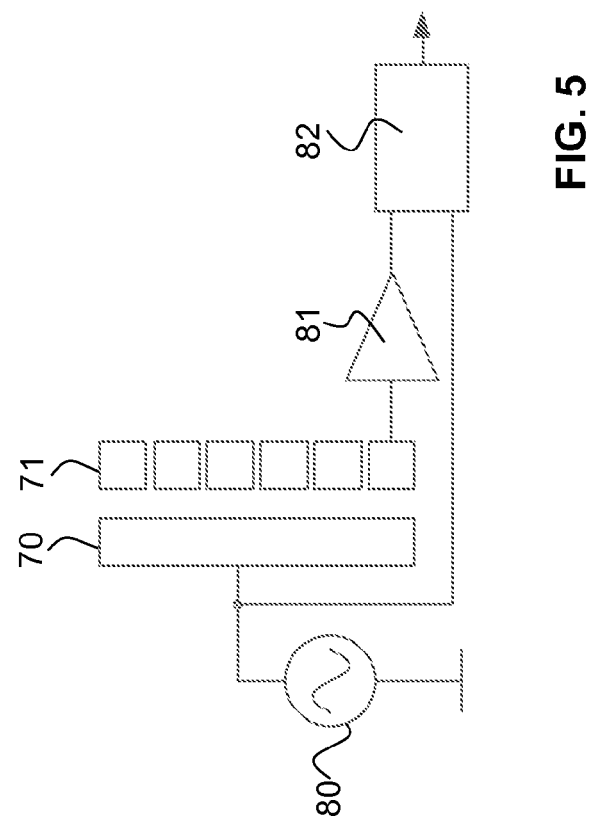
FIG. 5 shows a circuit diagram of the device according to the invention.

FIG. 5 shows a schematic representation of the measurement principle of the filling level sensor 7 according to the invention. A modulator 80 applies an excitation signal to the first electrode 70, the excitation signal is coupled capacitively into the second electrode 71. The coupled-in signal is fed as a measurement signal to a demodulator 82 via a preamplifier 81. The amplitude of the measurement signal is determined by the divider ratio of the capacitive voltage divider, which consists, on the one hand, of the coupling capacitance and, on the other hand, of the input capacitance of the sensor amplifier and of further parasitic capacitances. The coupling capacitance from transmitter electrode 70 to receiver electrode 71 depends on the distance between the electrodes and on the media located between the electrodes. Since the relative permeability of an aqueous solution is higher than that of air and plastic, the filling level in the container can be detected relatively precisely.

A sinusoidal signal is preferably applied as the excitation signal. The first frequencies applied are preferably in the range of 4 to 5 MHz, in particular of approximately 4 MHz or of 4.75 MHz. In a preferred variant, a second measurement frequency of approximately 100 kHz is additionally applied to the first electrode 70, particularly at low filling levels. This signal too is preferably a sinusoidal signal. The two different excitation signals are preferably applied alternately, but they can also be superposed.

The signal amplitude of this low frequency is greatly dependent on the properties, particularly the composition, of the fluid in the fluid collection container. By comparing the signal amplitudes on excitation with the first high and the second low frequency, conclusions can be made regarding the fluid in the collection container. In this way, it is possible to compensate for the influences of media even at low filling levels. Further, the filling level sensor 7 according to the invention can be used to detect properties, particularly the type or composition of the fluid. This information can be used, for example, for determining how or whether the pump is to be operated and/or for treatment of the patient.

As an alternative to a sinusoidal signal, it is possible to use a square signal or a triangular signal for the excitation. A phase measurement is also possible.

The above-described excitation with two different signals can also be used as the method according to the invention with other filling level sensors.

In addition, an inclination sensor can be arranged in the drainage pump unit according to the invention, particularly in the housing 1. The measurement signal can be corrected by means of this information, such that, even when the fluid collection container is in an inclined position, the information about the filling level determined in the container corresponds to the actual circumstances.

By virtue of the segmented electrode, the drainage pump unit according to the invention permits the production of inexpensive fluid collection containers while still ensuring a high degree of measurement accuracy.

The invention claimed is:

1. A drainage pump unit for aspirating body fluids by means of a suction pump, comprising:
   a suction pump housing comprising a wall with an inner face and an outer face,
   a suction pump being arranged in the suction pump housing,
   a fluid collection container being configured to be secured releasably on the suction pump housing,
   a capacitive filling level sensor being arranged on the suction pump housing for detecting a filling level in the fluid collection container without contacting the fluid in the fluid collection container, with at least two electrodes and a microprocessor, wherein a first of the at least two electrodes is in one piece, and at least a second of the at least two electrodes is segmented, and wherein the one-piece first electrode comprises a transmitter electrode and the segmented second electrode comprises a receiver electrode, and
   a modulator configured to apply an excitation signal to the one-piece first electrode,
   wherein the outer face of the wall of the suction pump housing faces towards the fluid collection container in an intended position of use,
   wherein the at least two electrodes and the microprocessor are arranged on a single printed circuit board,
   wherein the at least two electrodes are arranged at a distance from each other and extend along a common path,
   and wherein the printed circuit board is arranged on the inner face of the wall of the suction pump housing, such that the wall of the suction pump housing lies between the at least two electrodes and the fluid collection container in an intended position of use.

2. The drainage pump unit according to claim 1, wherein the excitation signal is coupled capacitively into the segmented second electrode.

3. The drainage pump unit according to claim 1, wherein the electrodes extend along approximately an entire fillable height of the fluid collection container.

4. The drainage pump unit according to claim 1, wherein the at least two electrodes are arranged next to each other in a common plane, or wherein the at least two electrodes lie opposite each other.

5. The drainage pump unit according to claim 1, wherein the at least one segmented electrode is divided into segments which are electrically insulated from one another and are arranged with a spacing of less than 1 mm between one another.

6. The drainage pump unit according to claim 1, further comprising an electronics system, wherein one of the electrodes is excited with an oscillating first signal from the electronics system.

7. The drainage pump unit according to claim 6, wherein the first signal includes a sinusoidal function.

8. The drainage pump unit according to claim 6, wherein the excitation takes place at a frequency in the range of 4 to 5 MHz.

9. The drainage pump unit according to claim 6, wherein the excitation takes place at a frequency of 4 MHz.

10. The drainage pump unit according to claim 6 wherein the excitation takes place at a frequency of 4.75 MHz.

11. The drainage pump unit according to claim 6, wherein the electronics system is configured to excite the excitable electrode with an oscillating second signal.

12. The drainage pump unit according to claim 11, wherein the excitation takes place at a frequency of approximately 100 kHz.

13. The drainage pump unit according claim 1, wherein the at least one segmented second electrode is divided into more than three segments.

14. The drainage pump unit according to claim 13, wherein the at least one segmented second electrode is divided into eight segments.

15. The drainage pump unit according to claim 1, wherein the at least two electrodes are band-shaped.

16. The drainage pump unit according to claim 1, wherein the at least two electrodes are copper-coated circuit boards.

17. The drainage pump unit according to claim 16, wherein the inner wall of the suction pump housing has a depression for receiving the at least two electrodes, said depression being so dimensioned that the at least two electrodes do not protrude from the inner wall in the direction of the container interior.

\* \* \* \* \*